United States Patent
Syed Abu Bakar et al.

(10) Patent No.: US 12,364,730 B2
(45) Date of Patent: Jul. 22, 2025

(54) COMPOSITION COMPRISING OIL PALM PHENOLICS FOR USE IN THE TREATMENT AND PREVENTION OF COLON DISEASES AND FOR PROMOTING AND MAINTAINING GUT AND GENERAL HEALTH

(71) Applicant: MALAYSIAN PALM OIL BOARD (MPOB), Kajang (MY)

(72) Inventors: Syed Fairus Syed Abu Bakar, Selangor (MY); Ravigadevi Sambanthamurthi, Selangor (MY); Yew Ai Tan, Selangor (MY); Mahinda Abeywardena, Selangor (MY)

(73) Assignee: MALAYSIAN PALM OIL BOARD (MPOB), Selangor (MY)

( * ) Notice: Subject to any disclaimer, the term of this patent is extended or adjusted under 35 U.S.C. 154(b) by 0 days.

(21) Appl. No.: 18/639,748

(22) Filed: Apr. 18, 2024

(65) Prior Publication Data

US 2024/0285718 A1    Aug. 29, 2024

Related U.S. Application Data

(62) Division of application No. 17/279,053, filed as application No. PCT/MY2019/050043 on Aug. 16, 2019.

(30) Foreign Application Priority Data

Aug. 17, 2018  (MY) .......................... PI 2018702907

(51) Int. Cl.
*A61K 36/889* (2006.01)
*A61P 1/14* (2006.01)

(52) U.S. Cl.
CPC .............. *A61K 36/889* (2013.01); *A61P 1/14* (2018.01); *A61K 2236/15* (2013.01)

(58) Field of Classification Search
None
See application file for complete search history.

(56) References Cited

U.S. PATENT DOCUMENTS

| | | |
|---|---|---|
| 2007/0259059 A1 | 11/2007 | Eidenberger |
| 2012/0269790 A1 | 10/2012 | Penalver Mellado et al. |
| 2015/0196614 A1 | 7/2015 | Manickam et al. |

FOREIGN PATENT DOCUMENTS

| | | |
|---|---|---|
| EP | 2953639 A1 | 12/2015 |
| WO | 2010/137939 A1 | 12/2010 |

OTHER PUBLICATIONS

Eid, N., et al., The impact of date palm fruits and their component polyphenols, on gut microbial ecology, bacterial metabolites and colon cancer cell proliferation, J. Nutr. Sci., 3 (2014) pp. 1-9. (Year: 2014).*
Eid, N.M.S., et al., Effect of Cultivar Type and Ripening on the Polyphenol Content of Date Palm Fruit, J. Agric. Food Chem., 61 ( 2013) pp. 2453-2460. (Year: 2013).*
Eid, N. et al., "The impact of date palm fruits and their component polyphenols, on gut microbial ecology, bacterial metabolites and colon cancer cell proliferation" Journal of Nutritional Science, Oct. 8, 2014, vol. 3, pp. 1-9.
Eid, N. M. S et al., "Effect of Cultivar Type and Ripening on the Polyphenol Content of Data Palm Fruit" Journal of Agricultural and Food Chemistry, Feb. 14, 2013, vol. 61, No. 10, pp. 2453-2460.
International Search Report and Written Opinion in Application No. PCT/MY2019/050043 dated Dec. 23, 2019.

* cited by examiner

*Primary Examiner* — Dominic Lazaro
(74) *Attorney, Agent, or Firm* — Maschoff Brennan

(57) ABSTRACT

The present invention relates to a composition for the treatment of colon disorder comprising oil palm polyphenolics (OPP) and fibres extracted from the vegetation liquor generated during the milling and extraction of oil from the oil palm fruit administered to a patient in an effective concentration of 50 mg gallic acid equivalents (GAE). The present invention further relates to a method of treatment and prevention of colon disorders and maintenance of gut health.

3 Claims, No Drawings

COMPOSITION COMPRISING OIL PALM PHENOLICS FOR USE IN THE TREATMENT AND PREVENTION OF COLON DISEASES AND FOR PROMOTING AND MAINTAINING GUT AND GENERAL HEALTH

BACKGROUND

Technical Field of Invention

The embodiments herein generally relate to composition from the vegetation liquor of palm oil milling comprising but not confined to oil palm phenolics and particularly to composition and methods of treatment and prevention of diseases related to large intestines. The embodiments herein more particularly relate to composition for the improvement of gut health and treatment, prevention and use in colon disorders and method of synthesizing the same.

Description of Related Art

*E. guineensis* is a major source of oil for human food uses, and also for secondary industrial uses. It is an important part of several local nutrition and customs, and a significant product of global commercial importance. Palm oil is an edible vegetable oil derived from the mesocarp (orange pulp) of the fruit of the oil palms, primarily oil palm *Elaeis guineensis*, and to a lesser extent from the American oil palm *Elaeis oleifera* and the maripa palm *Attalea maripa*.

The oil palm fruit mesocarp is a rich source of natural anti-oxidants, including carotene and vitamin E, and contains a range of beneficial compounds, including fibres, which are being characterised for usage in treatment and prevention of various health related issues. There is growing evidence that the consumption of plant polyphenols can have many health benefits in humans and oil palm fruit may be a rich source of these molecules.

While palm oil is known to provide health benefits, the extracts from vegetation liquor or aqueous stream of palm oil milling too have been proven to provide numerous benefits.

EP2953639 discloses Methods, compositions and kits for the prevention and treatment of mitochondrial dysfunction, mitochondrial DNA damage and genomic DNA damage are provided. The methods use the administration of palm fruit juice and/or compositions containing phenolic compounds present in palm fruit juice. The methods, compositions, and kits can be used to reduce DNA damage in subjects being treated with nucleoside reverse transcriptase inhibitors, such as patients having HIV or AIDS.

US20150196614A1 discloses composition and methods for prevention and treatment of cancer comprising compounds extracted from Palm oil mill effluent. Similarly, use of compositions comprising vegetation liquor extracts and/or oil palm phenolics for treatment of several metabolic disorders and diseases have been disclosed in the literature particularly obesity, diabetes, Alzheimer's and several viral infections too.

Dietary fibres are important components of a healthy diet and the oil palm fruit is likely to be a rich source of dietary fibres which have yet to be characterised or examined for their in vivo benefits. One of the most widely recognised benefits of dietary fibre is the strong association with reduced risk of colorectal cancer. The beneficial effects on the large bowel can depend on the type of fibre consumed and include dilution of toxins by increasing faecal bulk and increasing numbers and activities of beneficial microbes, such as those which generate short chain fatty acids (SCFA). Resistant starch (RS), defined as starch which escapes digestion in the small intestine and reaches the large bowel, is a form of dietary fibre that is highly effective in stimulating the production of SCFA and as a consequence has multiple beneficial effects on gut tissues. Experimental studies have demonstrated that dietary RS can protect against chemically-induced colorectal tumours and diet-induced colon DNA damage, and even protect against tissue damage and inflammation associated with colitis.

In view of foregoing, there exists an opportunity develop composition comprising natural ingredients that treat and prevent gut disorders and diseases, and promote gut and bowel health in humans.

SUMMARY OF THE INVENTION

Thus, the primary object of the embodiments herein is to provide a composition derived from the vegetation liquor (aqueous stream) of palm oil milling comprising but not confined to oil palm phenolics and fibres for gut health and the treatment of gut or colon disorders. The composition is interchangeably known as Oil Palm Phenolics (OPP) or palm fruit juice (PFJ).

Another object of the embodiments herein is to provide a composition rich in polyphenols extracted from the vegetation liquor generated during the milling and extraction of oil from the oil palm fruit bunches.

Yet another object of the embodiments herein is to provide a composition known as OPP comprising but not confined to oil palm phenolics and fibres used for gut health and the treatment and prevention of large intestinal disorders.

According to the embodiments herein, OPP a composition for gut health and the treatment of colon disorder comprises oil palm phenolics and fibres extracted from the vegetation liquor generated during the milling and extraction of oil from the oil palm fruit administered to a patient in an effective minimum concentration of 50 gallic acid equivalents (GAE). The composition is administered as a beverage, powder or health supplement.

According to an embodiment herein, the composition improves gut health and inhibits the colorectal cancer (CRC) by causing lesser colon DNA damage and increasing mucus barrier protection in large intestine of the patient.

According to an embodiment herein, the composition increases acetate, propionate and cecal butyrate concentration in large intestine of the patient.

According to an embodiment herein, the composition increases a number of cecal digesta bacteria in large intestine of the patient, wherein the bacteria include but are not confined to *Faecalibacterium prausnitzii, Akkermansia muciniphila* and *Ruminococcus gnavus*.

According to another embodiment herein, a method for treatment of colon disorder by administering a therapeutically effective amount of OPP, a composition comprising but not confined to oil palm phenolics and fibres extracted from the vegetation liquor generated during the milling and extraction of oil from the oil palm fruit, wherein the therapeutically effective amount of composition is minimum 50 gallic acid equivalents (GAE), wherein the composition is administered along with food or with drinking water.

According to an embodiment herein, the composition increases acetate, propionate and cecal butyrate concentration in large intestine of a patient.

According to an embodiment herein, the composition increases a number of cecal digesta bacteria in large intestine of a patient, wherein the bacteria include but are not confined to *Faecalibacterium prausnitzii, Akkermansia muciniphila* and *Ruminococcus gnavus.*

According to another embodiment herein, a method of inhibiting occurrence of colorectal cancer (CRC) in a person by reducing or preventing colon DNA damage and increasing mucus barrier protection using OPP, a composition comprising but not confined to oil palm phenolics and fibres extracted from the vegetation liquor generated during the milling and extraction of oil from the oil palm fruit.

According to an embodiment herein, a method of prevention of occurrence of colon disorders by administering a composition in a patient wherein the composition OPP comprises but is not confined to oil palm phenolics and fibres extracted from the vegetation liquor generated during the milling and extraction of oil from the oil palm fruit bunches, and wherein the composition increases cecal digesta mass of large intestine of a patient.

According to an embodiment herein, the composition increases cecal digesta concentrations of total SCFA in large intestine of a patient from.

According to an embodiment herein, the composition increases acetate, propionate and cecal butyrate concentration in large intestine of a patient.

According to an embodiment herein, the composition increases the number of mucus-producing goblet cells per colon crypt in large intestine of a patient.

According to an embodiment herein, the composition increases a number of cecal digesta bacteria in large intestine of a patient, wherein the bacteria include *Faecalibacterium prausnitzii, Akkermansia muciniphila* and *Ruminococcus gnavus.*

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide a composition rich in oil palm phenolics and fibres extracted from the vegetation liquor generated during the milling and extraction of oil from the oil palm fruit bunches. The composition inhibits the colorectal cancer (CRC) by reducing or preventing colon DNA damage and increasing mucus barrier protection. The embodiment, essentially, provides a method of treatment and prevention of gut diseases and disorders caused by administering composition comprising OPP extracts. In an embodiment, the OPP extracts are derived from vegetation liquor, the aqueous stream of the palm oil mill effluents. The embodiment also provides the composition for promoting gut health. The composition is either administered in a pharmaceutical, nutraceutical or supplement dosage form. In yet another embodiment, the use of OPP extracts for treatment or prevention of gut diseases and for promoting gut health is provided.

OPP extracted from the vegetation liquor, a composition rich in phenolics and fibres, reach the large intestines, and get metabolized by the resident bacteria and give rise of modified phenolic products. A proportion of these modified phenolic products then reach general circulation. The formation of bioactive metabolites by action of intestinal microbes contribute significantly to the effects of polyphenols. Consequently, the ingested forms of polyphenols and their metabolites come in contact with tissues in both the small and large intestine as well as reach general circulation, thereby potentially impacting the health of gut and distant tissues.

The gut microbes play a vital role in maintaining gut health and also in mediating the health of tissues distant to the gut through mechanisms such as modulation of the immune system. The microbes could produce signalling molecules that have a positive effect on the immune system and health in general.

In an embodiment, a method of promoting gut health by administering the composition by increasing number of cecal digesta bacteria in large intestine is provided. The bacteria usually include but are not confined to *Faecalibacterium prausnitzii, Akkermansia muciniphila* and *Ruminococcus gnavus.*

According to the embodiments herein, OPP, a composition for the treatment or prevention of colon disorder comprises oil palm phenolics and fibres extracted from the vegetation liquor generated during the milling and extraction of oil from the oil palm fruit bunches administered to a patient in an effective concentration of minimum 50 mg gallic acid equivalents (GAE). The composition is administered to the patient along with food or with drinking water.

According to an embodiment herein, the composition inhibits the colorectal cancer (CRC) by causing lesser colon DNA damage and increasing mucus barrier protection in large intestine of the patient.

According to an embodiment herein, the composition provides treatment and prevention of colon disorders by increasing cecal digesta mass in large intestine of the patient.

According to an embodiment herein, the composition increases cecal digesta concentrations of total SCFA in large intestine of the patient.

According to an embodiment herein, the composition increases acetate, propionate and cecal butyrate concentration in large intestine of the patient.

According to an embodiment herein, the composition increases the number of mucus-producing goblet cells per colon crypt in large intestine of the patient.

According to an embodiment herein, the composition increases a number of cecal digesta bacteria in large intestine of the patient, wherein the bacteria include but are not confined to *Faecalibacterium prausnitzii, Akkermansia muciniphila* and *Ruminococcus gnavus.*

According to another embodiment herein, a method for treatment of colon disorder by administering a therapeutically effective amount of OPP, a composition comprising oil palm phenolics and fibres extracted from the vegetation liquor generated during the milling and extraction of oil from the oil palm fruit bunches, wherein the therapeutically effective amount of composition is minimum 50 gallic acid equivalents (GAE), wherein the composition is administered along with food or with drinking water.

According to an embodiment herein, the composition increases cecal digesta concentrations of total SCFA in large intestine of a patient.

According to an embodiment herein, the composition increases acetate, propionate and cecal butyrate concentration in large intestine of a patient.

According to an embodiment herein, the composition increases the number of mucus-producing goblet cells per colon crypt in large intestine of a patient.

According to an embodiment herein, the composition increases a number of cecal digesta bacteria in large intestine of a patient, wherein the bacteria include but are not confined to *Faecalibacterium prausnitzii, Akkermansia muciniphila* and *Ruminococcus gnavus*.

According to another embodiment herein, a method of inhibiting occurrence of colorectal cancer (CRC) in a person by reducing or preventing colon DNA damage and increasing mucus barrier protection using OPP, a composition comprising oil palm but not confined to phenolics and fibres extracted from the vegetation liquor generated during the milling and extraction of oil from the oil palm fruit bunches.

According to an embodiment herein, a method of prevention of occurrence of colon disorders by administering a composition in a patient wherein the composition OPP comprises but not confined to oil palm phenolics and fibres extracted from the vegetation liquor generated during the milling and extraction of oil from the oil palm fruit bunches, and wherein the composition increases cecal digesta mass of large intestine of a patient.

According to an embodiment herein, the composition increases cecal digesta concentrations of total SCFA in large intestine of a patient.

According to an embodiment herein, the composition increases acetate, propionate and cecal butyrate concentration in large intestine of a patient.

According to an embodiment herein, the composition increases the number of mucus-producing goblet cells per colon crypt in large intestine of a patient.

According to an embodiment herein, the composition increases a number of cecal digesta bacteria in large intestine of a patient, wherein the bacteria include but are not confined to *Faecalibacterium prausnitzii, Akkermansia muciniphila* and *Ruminococcus gnavus*.

In an embodiment, OPP or extracts of vegetation liquor may be administered alone or in combination with other additives in the form of a pharmaceutical, nutraceutical or supplemental composition. The said composition may include bioactive lipid- and water-soluble compounds wherein the water-soluble compounds primarily comprising phenolics, shikimic acid, and soluble fibre and the phenolic compounds primarily comprising p-hydroxybenzoic acid and three caffeoylshikimic acid isomers.

In another embodiment, the composition can be administered preferably orally in acceptable dosage forms.

In yet another embodiment, the composition includes a pharmaceutically acceptable carrier, preservative agent, sweetener, aqueous carrier, flavoring agent, coloring agent, and a combination thereof.

In yet another embodiment, the pharmaceutically acceptable carrier may include stabilizers, carriers, extenders, and other suitable substances. The pharmaceutically acceptable carrier further includes one or more selected from the group consisting of: water, saline, starches, sugars, gels, lipids, waxes, glycerol, solvents, oils, liquids, proteins, glycols, electrolyte solutions, alcohols, fillers, binders, emulsifiers, humectants, preservatives, buffers, colorants, emollients, foaming agents, sweeteners, thickeners, surfactants, additives and solvents and mixtures thereof.

The composition is made suitable for oral, injectable or external administration and further comprises the form of a solid, liquid, powder, paste, gel, tablet, granule, foam, pack, aerosol, solvent, diluent, capsule, pill, drink, liposome, syrup, solution, suppository, emulsion, enema, suspension, dispersion, food, bio-delivery agents and mixtures thereof.

The form used to deliver the treatment to a human or animal is all inclusive not limited to a cream, solid, liquid, powder, paste, gel, tablet, granule, foam, pack, ointment, aerosol, solvent, tablet, diluent, capsule, pill, drink, liposome, syrup, solution, suppository, emulsion, suspension, dispersion, food, bolus, electuary, paste or other bio-delivery system or agent.

The compositions of the present embodiment include pharmaceutically acceptable carriers and delivery systems adapted for varying route of administration such as topical, enteral and parenteral including but not limited to: oral, rectal, nasal, vaginal, subcutaneous, intramuscular, intravenous, intratumor, intraperitoneal, intramammary, intraosseous infusion, transmucosal, transdermal, epicutaneous, intracutaneous, epidural, intrathecal, inhalation, opthalamic or other suitable route.

Compositions for administration include aqueous and non-aqueous isotonic sterile solutions, which may contain anti-oxidants, oils, glycols, alcohols, buffers, bacteriostats, solutes, suspending agents, biodegradable time-release polymers, surfactants, preservatives and thickening agents.

Compositions of the present invention adapted for oral administration may contain a predetermined quantity of the active ingredient i.e. palm fruit juice or its fractions and take the form of sprays, liquids, syrups, beverages, capsules, powders, granules, solutions, suspensions, tablets, food, lozenges or any other form in which the active ingredients are taken by mouth and absorbed through the alimentary canal.

Compositions may also incorporate the active ingredients with pharmaceutically acceptable carriers such as buffers, gums, surfactants, fillers, preservatives, bulking agents, colorants, diluents, flavoring agents, emulsifiers, sugars, oils, cellulose, gelatin, flour, maltodextrose, time release polymers and the like.

In another embodiment the oral composition comprises one or more additional oral active ingredients selected from the group consisting of: orally acceptable vehicles, anti-tartar agents, antibacterial agents, anti-inflammatory agents, anticaries agents, whitening agents, densensitizing agents, vitamins, compatible enzymes, chlorophyll compounds, periodontal actives, breath freshening agents, malodour control agents, salivary stimulants and combinations thereof.

In another embodiment, wherein the orally acceptable vehicle comprises one or more components selected from the group consisting of: viscosity modifiers, diluents, surface active agents, pH modifying agents, abrasives, humectants, mouth feel agents, sweetening agents, flavor agents, colorants, preservatives, and combinations thereof.

It will be appreciated by those skilled in the art that the pharmacological effective concentration of the herbal extract-based composition in the formulation will depend on other ingredients in the formulation, the mode of administration of the formulation, the physiologic site to be treated, and the desired health promoting or therapeutic effect to be provided, In another embodiment, the composition may be incorporated into a tablet (including capsule, caplet, and the like). Suitable bases are known to those skilled in the art to include fillers, binders, coatings, excipients and combinations thereof. For example, base ingredients include, but are not limited to, plant cellulose, natural silica, magnesium stearate, wax, vegetable glycerides, vegetable stearate, and a combination thereof.

In an embodiment, the composition is used to maintain the colon and gut health by administering the composition as a nutraceutical or diet supplement. In another embodiment, the composition is used to prevent colon and gut disorders and diseases by administering the composition as a nutraceutical or diet supplement.

Experimental Details

According to the present invention, in order to investigate the beneficial effects of the composition for the treatment and prevention of gastro-intestinal disorder or colon disorders, and maintenance of gut health, the below experiments were conducted on rats.

Rats were fed with the composition comprising OPP obtained from the vegetation liquor generated during the milling and extraction of oil from the oil pam fruit bunches, according to the present invention, and examined for the potential of its constituents to benefit gut health. Specifically, it was examined whether the composition OPP comprising oil palm phenolics fibres and other components extracted from the vegetative liquor generated during the milling and extraction of oil from the oil palm fruit bunches, has benefits in a model where rats are fed a diet moderately high in cooked red meat but low in fibre, factors which have previously been shown to result in poor colon conditions, including higher levels of colon DNA damage and reduced mucus barrier protection, which potentially underlies gastrointestinal (GI) diseases such as colorectal cancer (CRC).

Materials and Methods

Animals and diets: 56 male Sprague-Dawley rats of ~200 g weight were obtained from the Animal Resource Centre, Murdoch University, Perth, Australia. The rats were housed in wire-bottomed cages in a room of controlled temperature (23° C.) and lighting (a 12 h light-dark cycle) and allowed free access to food and water. The rats were assigned randomly to 1 of 5 groups (n=10-13 per group) and fed the respective experimental diets for 4 wk. The dietary compositions as shown in Table 1 were based on the AIN-93 diet and contained 5% wheat bran as a fibre source. Diets contained 48% corn starch except for the Resistant starch (RS) supplemented diet which contained 18% corn starch and 30% high amylose maize starch (HAMS; Hi-maize™, National Starch Food Innovation, Australia). All diets contained 25% cooked red meat (premium beef mince). The fat used in the diets was sunflower oil (Crisco, Australia) which contained approximately 11% SFA, 20% MUFA and 69% PUFA. OPP was added to the western diet (WD) either in the food or OPP or green tea were added to the drinking water of rats receiving the WD diet and maintained at 50 mg gallic acid equivalent (GAE)/day (adjusted 3 times per week based on actual consumption). WD on its own served as the control.

TABLE 1

Composition of Experimental Diets (g/kg diet)[a]

| Variables | WD[b] | OPP-F[c] | HAMS[d] |
|---|---|---|---|
| red meat | 250 | 250 | 250 |
| cornstarch | 480 | 480 | 180 |
| Hi-maize ™ | 0 | 0 | 300 |
| sucrose | 100 | 100 | 100 |
| sunflower oil | 70 | 70 | 70 |
| wheat bran | 50 | 50 | 50 |
| 1-cystine | 3 | 3 | 3 |
| Choline bitartrate | 2.5 | 2.5 | 2.5 |
| vitamins (ain-93) | 10 | 10 | 10 |
| minerals | 35 | 35 | 35 |
| tert-butyl hydroquinol | 0.014 | 0.014 | 0.014 |
| OPP GAE/kg diet | | 2000 | |

With respect to Table 1, [a]Diets were based on AIN-93 (G) formulation. WD, Western diet control. [b] In addition to the Western diet control treatment OPP or green tea was added to the drinking water of rats receiving the WD diet for OPP-D or GT-treatments. [c]In another treatment OPP was added to the base formulation and was calculated on food consumption at 25 g/d to provide 50 mg GAE/d/rat. [d]High amylose maize starch.

The individual body weights of the rats were monitored throughout the study. At the completion of the dietary intervention period rats were anesthetized with 4% halothane/oxygen to allow collection and weighing of gut tissues and digesta at the time animals were killed. Fecal and cecal digesta was homogenized and divided into aliquots for various analyses and frozen at −80° C. Experimental procedures were approved by the animal ethics committee of CSIRO Food and Nutrition Flagship, and complied with the Australian code of practice for the care and use of animals for scientific purposes.

SCFA, Phenols, p-Cresol and Ammonia

Digesta was thawed and the liquid phase distilled with heptanoic acid added as internal standard (at 1.68 μmol/mL), followed by separation of SCFA in the distillate using gas liquid chromatography. The total SCFA was calculated as the sum of acetic, propionic, butyric, isobutyric, caproic, isovaleric, and valeric acids. Pools represent the total amount of a given component in the digesta collected from within the cecum or the colon. Levels are based on amounts in the wet weight of digesta.

Microbiota

DNA was extracted from thawed digesta by a process involving repeated bead beating in the presence of high concentrations of SDS, salt and EDTA, followed by purification using QIAamp columns. Purified DNA was quantified using a Thermo Scientific Nanodrop 2000 Spectrophotometer (Thermo Fisher Scientific, Wilmington, DE, USA). Numbers of target bacteria were estimated using quantitative real-time PCR using a CFX Connect 96 real-time PCR detection system and CFX Manager v2.1 (Bio-Rad, CA, USA). An 8-series of 10-fold dilutions of a sample-derived standard containing the target amplicon were analysed in parallel with DNA samples for estimation of absolute abundance and PCR efficiency.

Histology

Tissue Collection and Processing

Colon length was measured and 0.5 cm of tissue at the distal and proximal end was discarded. Samples for histological assessment (2 cm) were taken at 8 cm from the distal end. Colon tissue was opened along the section length, cleaned of digesta, placed in histology cassettes, submerged in 10% neutral buffered formalin for 24 h and then stored in 70% ethanol until processing through graded levels of ethanol and chloroform before embedding in wax. Embedded tissues were cut into 5 μm sections and were stained for Statistical Analysis All values are expressed as the mean±standard error of mean (SEM). Comparisons were performed by one-way ANOVA followed by Tukey's multiple-comparison post hoc test. Differences were considered to be significant at P<0.05. Statistical analysis was performed using GraphPad Prism version 6.01 for Windows, GraphPad Software, La Jolla, California, USA.

Results

There were no significant differences in final body weight between the treatment groups (data not shown) or weights of organs. Table 2 shows the data with respect to the effects of dietary treatment on final body, organ, gut tissue and digesta weights and digesta pH in rats.

TABLE 2

Effects of Dietary Treatment on Final Body, Organ, Gut Tissue and Digesta Weights, and Digesta pH in Rats[a]

| Variables | WD | OPP-F | OPP-D | HAMS | GT |
|---|---|---|---|---|---|
| body weight, g | 306 ± 9 | 318 ± 11 | 294 ± 11 | 287 ± 19 | 303 ± 9 |
| cecum | | | | | |
| tissue weight, g | 0.93 ± 0.18 | 0.72 ± 0.03 [a] | 0.79 ± 0.05 | 1.18 ± 0.08 [ab] | 0.61 ± 0.02 [b] |
| digesta weight, g | 1.86 ± 0.17 [ab] | 2.18 ± 0.21 [c] | 3.42 ± 0.37 [ade] | 4.82 ± 0.60 [bcef] | 1.48 ± 0.11 [df] |
| cecum pH | 7.94 ± 0.08 [a] | 7.82 ± 0.09 [b] | 7.68 ± 0.06 [c] | 6.91 ± 0.16 [abcd] | 7.69 ± 0.07 [d] |
| colon | | | | | |
| digesta weight, g | 0.96 ± 0.16 [a] | 1.43 ± .19 [b] | 1.40 ± 0.20 [c] | 3.37 ± 0.50 [abcd] | 1.68 ± 0.08 [d] |
| colon pH | 7.49 ± 0.08 [ab] | 7.85 ± 0.15 [cd] | 8.04 ± 0.09 [aef] | 6.44 ± 0.07 [bdfg] | 7.14 ± 0.06 [ceg] |
| organ weights, g | | | | | |
| liver | 11.33 ± 0.41 | 11.90 ± 0.52 | 11.27 ± 0.68 | 11.06 ± 0.65 | 10.55 ± 0.31 |
| heart | 1.17 ± 0.04 | 1.19 ± 0.04 | 1.14 ± 0.04 | 1.06 ± 0.05 | 1.20 ± 0.07 |
| kidney | 1.95 ± 0.07 | 2.10 ± 0.06 | 2.02 ± 0.08 | 1.86 ± 0.11 | 1.97 ± 0.05 | mucins using Alcian blue (neutral mucins) and periodic acid-Schiff's reagent (sulphomucins) in combination using previously described methods. Histology reagents were supplied by Sigma.

Histological Assessment

For wall thickness, 15-20 measurements were taken at different points along each section. Final wall thickness was reported as the average thickness (in μm) over the length of the wall.

Crypts were measured from the base of the muscularis mucosa to the luminal surface. Crypt cell height was also recorded as the number of columnar epithelial cells on one side of the crypt. The total number of columnar epithelial cells (both sides of the crypt) were counted and recorded from an average of 8-10 crypts per section.

Goblet cells in the crypt were counted and the total area of the goblet cells within each crypt was measured by drawing around each individual goblet cell and adding the areas together. Crypt cell area was calculated by drawing around individual crypts used for assessment. The total area of the goblet cells was expressed as a percentage of the crypt area. Goblet cells were recorded as containing either strongly sulphated mucins (pH<2.5, staining purple/magenta) or neutral mucins (pH>2.5, staining dark blue).

With respect to Table 2, [a]Values are mean±SEM for n=10-13 animals per group; WD, Western diet control; OPP-F, OPP added to diet; OPP-D, OPP added to drink; HAMS, high amylose maize starch in diet; GT, green tea added to drink. Common letters in the same row indicate significant differences, P<0.05.

Cecal digesta bulk (Table 2) was significantly increased relative to the WD group and also the GT group when OPP was consumed as a drink but not when added to the diet. The cecal bulk in rats consuming HAMS was significantly greater than in all other groups. Similarly, HAMS significantly increased the cecal tissue weights (Table 2) when compared to OPP and GT treatments.

The pH of the cecal digesta was lowered significantly relative to the WD group by HAMS but not by other treatments. In digesta from the colon pH was significantly lowered by HAMS relative to WD and both OPP treatments. Colon digesta pH was significantly higher than WD for OPP drink (Table 2).

Levels of individual and total SCFA in digesta (Table 3) were significantly influenced by treatment. Table 3 shows the effects of Dietary Treatment on Individual and Total SCFA in Cecal and Colon Digesta of Rats.

TABLE 3

Effects of Dietary Treatment on Individual and Total SCFA in Cecal and Colon Digesta of Rats[a]

| Variables | WD | OPP-F | OPP-D | HAMS | GT |
|---|---|---|---|---|---|
| Cecum concentration [b] | | | | | |
| acetate | 41.4 ± 3.6 [a] | 55.5 ± 4.4 | 55.5 ± 2.7 | 68.1 ± 4.9 [ab] | 40.1 ± 2.9 [b] |
| propionate | 6.0 ± 0.7 [ab] | 9.2 ± 0.9 [ac] | 9.5 ± 0.6 [bd] | 7.8 ± 0.8 | 5.1 ± 0.4 [cd] |
| butyrate | 4.0 ± 0.3 [a] | 6.2 ± 0.8 [abc] | 2.8 ± 0.3 [bd] | 3.5 ± 0.4 [c] | 5.1 ± 0.6 [d] |
| total | 53.4 ± 4.5 [ab] | 73.3 ± 0.6 [ac] | 69.3 ± 2.9 | 79.7 ± 5.6 [bd] | 51.9 ± 3.6 [cd] |
| Cecum pool [c] | | | | | |
| acetate | 73.2 ± 6.2 [ab] | 124.0 ± 17.7 [c] | 188.4 ± 19.5 [ade] | 328.9 ± 44.6 [bcef] | 60.4 ± 7.2 [df] |
| propionate | 11.4 ± 1.7 [ab] | 20.9 ± 3.4 [c] | 33.6 ± 4.3 [ad] | 37.9 ± 5.8 [bce] | 7.7 ± 1.0 [de] |
| butyrate | 7.1 ± 0.7 [ab] | 13.8 ± 2.1 [a] | 8.9 ± 0.9 [c] | 17.1 ± 2.6 [bcd] | 7.9 ± 1.5 [d] |
| total | 94.9 ± 8.4 [ab] | 164.1 ± 23.4 [c] | 235.9 ± 24.1 [ade] | 384.7 ± 51.4 [bcef] | 78.4 ± 9.6 [df] |
| Colon concentration | | | | | |
| acetate | 32.9 ± 3.6 [a] | 35.0 ± 2.4 [b] | 26.2 ± 3.0 [c] | 48.5 ± 4.3 [abcd] | 28.5 ± 1.7 [d] |
| propionate | 4.8 ± 0.4 | 6.5 ± 0.5 [ab] | 6.3 ± 0.4 [c] | 3.7 ± 0.6 [bc] | 4.4 ± 0.2 [a] |
| butyrate | 3.7 ± 0.5 [ab] | 3.0 ± 0.3 | 1.6 ± 0.2 [ac] | 2.0 ± 0.4 [b] | 3.7 ± 0.3 [c] |
| total | 42.8 ± 4.5 | 46.1 ± 2.9 | 35.9 ± 3.2 [a] | 54.2 ± 4.7 [ab] | 38.1 ± 1.8 [b] |
| Colon pool | | | | | |
| acetate | 33.1 ± 7.6 [a] | 50.3 ± 8.1 [b] | 35.6 ± 6.7 [c] | 170.9 ± 29.6 [abcd] | 47.9 ± 3.8 [d] |
| propionate | 4.8 ± 1.0 [a] | 9.8 ± 1.7 | 8.8 ± 1.4 | 11.8 ± 1.9 [a] | 7.4 ± 0.5 |
| butyrate | 3.3 ± 0.6 | 4.4 ± 0.8 | 2.3 ± 0.4 [a] | 6.6 ± 1.5 [a] | 6.2 ± 0.6 |
| total | 42.8 ± 9.4 [a] | 67.1 ± 10.7 [b] | 49.3 ± 8.4 [c] | 189.3 ± 31.5 [abcd] | 64.0 ± 4.4 [d] |

With respect to Table 3, [a]Values are mean±SEM for n=10-13 animals per group; WD, Western diet control; OPP-F, OPP added to diet; OPP-D, OPP added to drink; HAMS, high amylose maize starch in diet; GT, green tea added to drink; [b]Concentration is expressed as μmol/g digesta. [c]Pool is expressed as μmol. Common letters in the same row indicate significant differences, P<0.05.

In the cecum dietary OPP and HAMS significantly increased total SCFA concentration relative to WD and GT. Relative to WD acetate concentration was increased by HAMS, butyrate concentration was increased by dietary OPP, and propionate concentration was increased by dietary and drink OPP. When cecal SCFA pools were examined (the total amount present in the cecum) OPP drink and HAMS significantly increased total SCFA, acetate and propionate relative to WD and GT, with HAMS having significantly higher pools compared to all other treatments. In contrast, OPP diet (not drink) and HAMS significantly increased cecal butyrate pools relative to WD. SCFA levels in colon digesta were also influenced by treatment. OPP drink significantly lowered colon butyrate concentration relative to the WD treatment. HAMS significantly increased colon acetate concentration and lowered butyrate concentration relative to WD.

Protein fermentation products were also analysed in digesta and shown to be impacted by diet. Table 4 shows the effects of Dietary Treatment on Phenols, Cresols and Ammonia in Cecal and Colon Digesta of Rats.

TABLE 4

Effects of Dietary Treatment on Phenols, Cresols and Ammonia in Cecal and Colon Digesta of Rats[a]

| Variables | WD | OPP-F | OPP-D | HAMS | GT |
|---|---|---|---|---|---|
| cecum ammonia | | | | | |
| concentration[b] | 7.97 ± 0.47 [a] | 8.38 ± 0.99 [b] | 5.76 ± 0.45 | 4.19 ± 0.6 [abc] | 7.76 ± 0.62 [c] |
| pool[c] | 15.26 ± 2.10 | 17.58 ± 1.78 | 18.89 ± 1.87 | 20.89 ± 3.77 | 11.96 ± 1.66 |
| cecum phenols | | | | | |
| concentration | 0.68 ± 0.04 [ab] | 6.04 ± 1.02 [acd] | 5.55 ± 0.60 [bef] | 0.52 ± 0.02 [df] | 0.63 ± 0.02 [ce] |
| cecum cresols | | | | | |
| concentration | 5.71 ± 0.93 [a] | 8.12 ± 1.66 [bc] | 3.62 ± 0.77 [b] | 2.64 ± 0.49 [acd] | 6.90 ± 0.73 [d] |

TABLE 4-continued

Effects of Dietary Treatment on Phenols, Cresols and Ammonia in Cecal and Colon Digesta of Rats[a]

| Variables | WD | OPP-F | OPP-D | HAMS | GT |
|---|---|---|---|---|---|
| colon ammonia | | | | | |
| concentration | 10.59 ± 0.58 [a] | 9.06 ± 0.71 [b] | 6.59 ± 0.47 [d] | 5.10 ± 0.55 [abc] | 12.19 ± 0.31 [cd] |
| pool[b] | 12.70 ± 1.82 | 13.89 ± 1.6 | 9.34 ± 1.56 [ab] | 17.67 ± 3.00 [b] | 20.53 ± 1.17 [a] |
| colon phenols | | | | | |
| concentration | 0.96 ± 0.07 [a] | 3.02 ± 0.34 [abcd] | 1.65 ± 0.17 [bc] | 0.5 ± 0.01 [de] | 0.83 ± 0.06 [c] |
| colon cresols | | | | | |
| concentration | 14.9 ± 3.02 [a] | 9.98 ± 2.18 [b] | 13.74 ± 3.51 [c] | 1.54 ± 0.23 [bd] | 24.05 ± 3.4 [acd] |

With respect to Table 4, [a]Values are mean±SEM for n=10-13 animals per group. WD, Western diet control; OPP-F, OPP added to diet; OPP-D, OPP added to drink; HAMS, high amylose maize starch in diet; GT, green tea added to drink. [b]Concentration is expressed as μmol/g digesta. [c]Pool is expressed as μmol. Common letters in the same row indicate significant differences, P<0.05.

Ammonia concentration was significantly lowered by HAMS in both the cecum and colon when compared with the WD group. OPP drink significantly lowered colon ammonia concentration relative to the green tea treatment. No treatments had effects relative to WD when cecal or colon ammonia pools were calculated. Concentrations of phenols in the cecum were increased significantly by both OPP treatments and increased significantly in the colon by dietary OPP (with a trend of increased concentration by drink OPP). Concentrations of p-cresol were significantly lowered by HAMS relative to WD in the cecum and in the colon.

Dietary treatment had a significant impact on the composition of bacterial populations in the cecal digesta, although total numbers of bacteria/g of digesta did not differ significantly between the treatments. Table 5 shows the effects of Dietary Treatment on Numbers of Caecal Bacteria.

With respect to Table 5, [a]Values are expressed as $\log_{10}$ bacteria/g digesta (mean±SEM) for n=10-13 animals per group. WD, Western diet control; OPP-F, OPP added to diet; OPP-D, OPP added to drink; HAMS, high amylose maize starch in diet; GT, green tea added to drink. Common letters in the same row indicate significant differences, P<0.05.

When rats consumed OPP as a drink, some significant effects on targeted microbial populations relative to the HR diet alone were observed. That is, OPP drink increased numbers of Faecalibacterium prausnitzii, Akkermansia muciniphila and Ruminococcus gnavus. The positive control, HAMS, elicited the greatest number of changes in the microbiota, significantly increasing (relative to HR alone) numbers of Ruminococcus bromii, the Clostridium leptum group, Bifidobacterium, A. muciniphila and Ruminococcus torques. Bacteria of the genus Roseburia decreased in number in response to HAMS. Numbers of Lactobacillus were increased by GT but not by OPP or by HAMS, and numbers of Bacteroides were significantly higher for OPP drink when compared to GT.

There were no significant differences in the numbers of colon DNA single strand breaks between treatments (data not shown).

TABLE 5

Effects of Dietary Treatment on Numbers of Caecal Bacteria[a]

| | WD | OPP-F | OPP-D | HAMS | GT |
|---|---|---|---|---|---|
| A. muciniphila | 8.92 ± 0.21 [ab] | 9.49 ± 0.28 [c] | 10.72 ± 0.20 [bcd] | 10.11 ± 0.14 [a] | 9.67 ± 0.20 [d] |
| Bacteroides | 10.54 ± 0.24 | 10.07 ± 0.34 | 11.23 ± 0.29 [a] | 10.70 ± 0.14 | 9.48 ± 0.45 [a] |
| Bifidobacterium | 9.84 ± 0.22 [a] | 9.09 ± 0.27 [be] | 9.53 ± 0.15 [cf] | 11.87 ± 0.16 [abcd] | 10.39 ± 0.22 [def] |
| C. coccoides | 7.83 ± 0.09 | 7.99 ± 0.09 | 8.18 ± 0.09 | 8.11 ± 0.08 | 8.05 ± 0.09 |
| C. leptum | 6.99 ± 0.13 [a] | 7.25 ± 0.11 | 7.25 ± 0.11 | 7.72 ± 0.12 [ab] | 7.19 ± 0.14 [b] |
| E. coli | 7.41 ± 0.23 | 7.02 ± 0.31 | 6.64 ± 0.34 | 6.51 ± 0.32 | 7.39 ± 0.17 |
| E. faecium | 6.20 ± 0.50 | 6.92 ± 0.77 | 6.54 ± 0.16 | 6.82 ± 1.06 | 6.38 ± 0.75 |
| F. prausnitzii | 10.29 ± 0.24 [a] | 10.15 ± 0.24 [b] | 11.65 ± 0.32 [abc] | 10.84 ± 0.24 | 10.51 ± 0.18 [c] |
| Lactobacillus | 7.13 ± 0.10 [a] | 7.33 ± 0.16 [b] | 7.44 ± 0.13 [c] | 7.62 ± 0.15 | 8.07 ± 0.12 [abc] |
| R. bromii | 9.18 ± 0.34 [ab] | 9.76 ± 0.27 [c] | 9.70 ± 0.21 [d] | 11.19 ± 0.28 [acd] | 10.35 ± 0.23 [b] |
| R. gnavus | 9.40 ± 0.13 [a] | 9.48 ± 0.11 [c] | 10.33 ± 0.09 [abcd] | 9.71 ± 0.10 [b] | 9.79 ± 0.18 [d] |
| R. torques | 8.76 ± 0.22 [a] | 9.13 ± 0.19 [b] | 8.75 ± 0.26 [c] | 10.48 ± 0.18 [abcd] | 9.18 ± 0.42 [d] |
| Roseburia | 7.04 ± 0.14 [a] | 6.71 ± 0.19 | 6.51 ± 0.08 | 6.22 ± 0.20 [ab] | 6.90 ± 0.14 [b] |
| SRB dsr | 7.96 ± 0.15 | 8.25 ± 0.10 | 8.33 ± 0.08 | 8.12 ± 0.10 | 8.22 ± 0.15 |
| Total Bacteria | 11.63 ± 0.09 | 11.62 ± 0.12 | 11.62 ± 0.09 | 11.99 ± 0.09 | 11.76 ± 0.09 |

Histological analysis of colon tissue (Table 6) revealed no changes in the thickness of the muscularis layer (data not shown) but some changes in the epithelial layer. Table 6 shows the effects of Dietary Treatment on Colon Tissue Goblet Cell Numbers.

TABLE 6

Effects of Dietary Treatment on Colon Tissue Goblet Cell Numbers[a]

| | WD | OPP-F | OPP-D | HAMS | GT |
|---|---|---|---|---|---|
| Wall thickness (μm) | 460 ± 29 | 400 ± 31 | 383 ± 34 | 366 ± 24 | 407 ± 60 |
| Total cells per crypt[b] | 61 ± 2 [a] | 61 ± 2 [b] | 63 ± 1 [c] | 73 ± 2 [abcd] | 64 ± 2 [d] |
| Goblet cells per crypt | | | | | |
| Total | 6.3 ± 0.6 [ab] | 8.4 ± 0.5 [ac] | 9.5 ± 0.6 [d] | 15.0 ± 0.6 [bcde] | 8.4 ± 1.0 [e] |
| Sulphomucin positive | 0.8 ± 0.2 | 1.1 ± 0.3 | 0.9 ± 0.4 | 0.7 ± 0.3 | 0.9 ± 0.3 |
| Neutral mucin positive | 5.5 ± 0.6 [ab] | 7.3 ± 0.5 [c] | 8.6 ± 0.6 [ad] | 14.3 ± 0.9 [bcde] | 7.5 ± 1.0 [e] |
| Area (% of crypt) | 9.2 ± 0.9 [a] | 11.7 ± 0.8 | 13.8 ± 1.2 [a] | 12.5 ± 0.6 | 11.8 ± 1.7 |

With respect to Table 6, [a]Values are mean±SEM for n=10-13 animals per group. WD, Western diet control; OPP-F, OPP added to diet; OPP-D, OPP added to drink; HAMS, high amylose maize starch in diet; GT, green tea added to drink. [b]Total number of epithelial cells per crypt (8-10 crypts per section). Common letters in the same row indicate significant differences, P<0.05.

The total number of cells and the number of mucus-producing goblet cells per colon crypt was significantly higher for HAMS relative to all other treatments. OPP drink also significantly increased the number of goblet cells producing neutral mucins per crypt compared to WD. When the goblet cell number was represented as a percentage of crypt cells then only OPP drink significantly altered (increased) the percentage relative to WD.

Discussion

Thus, the present invention, examined whether a polyphenol-rich, fibre-containing extract from a vegetation liquor generated from the processing of the oil palm can have some GI benefits in rats consuming a western-type diet. Results show that OPP consumption had a range of effects consistent with promotion of GI health. These include increased digesta mass, increased production of SCFA, shifts in digesta microbiota populations that are suggestive of benefit, and increase in mucus-producing goblet cells within colon crypts. These effects were in many instances similar to those induced by dietary HAMS, a commercial source of RS known to have multiple benefits to the large bowel. There were no obvious detrimental effects of OPP on gut health. Consequently, there is potential for development of OPP or its constituents for use in humans to promote bowel health.

Consumption of dietary fibres has long been known to be associated with reduced risk of colorectal diseases, especially cancer, and this reduced risk occurs through multiple mechanisms which can be dependent on the type of fibre. A primary means of benefit occurs as a result of promotion of stool bulk which acts to dilute toxins and assist their excretion. Increased stool bulk occurs through a combination of the water holding capacity of the fibres and increased microbial mass resulting from use of some fibres as substrates. In the present invention, it is shown that OPP increased digesta mass in rats, suggesting fibre-like effects and that OPP may have stool bulking capability if it or a fibre-rich component were to be consumed by humans.

Another mechanism through which dietary fibres may protect against colorectal disease is by production of SCFA through microbial fermentation. Highly fermentable fibres, such as RS, can generate significant amounts of the main forms of SCFA, namely acetate, butyrate and propionate, and these in turn have multiple effects and benefits. In addition to providing the main sources of energy for cells lining the colon they also act to stimulate apoptosis of damaged cells, stimulate the immune system, and enhance gut barrier function via a mechanism that includes enhanced mucus production. In the present invention, OPP consumption has resulted in greater SCFA production and increased the number of cells that produce mucus in the colon epithelium, again suggestive of fibre-like activity and potential for protection against colorectal disease in humans. Dietary RS and other fibres have been shown to protect against colon DNA damage induced by a western style diet in a rodent model and there is evidence that they can protect against oncogenic processes in the colon of humans consuming a diet high in red meat through a mechanism that may partly involve the SCFA. However, in the present invention, any evidence of a significant alteration in levels of colon DNA damage was not seen with any of the treatments.

One of the most promising findings of the present invention relates to the effects of OPP on the composition of gut microbiota populations. There is a growing recognition of the important role that gut microbes play in GI health and also in mediating the health of tissues distant to the gut through mechanisms such as modulation of the immune system. Microbial products, such as butyrate, appear to have an important role in facilitating these effects. Consequently, there is a significant global effort to understand the still relatively uncharacterized activities and roles of the many hundreds of microbial species within the gut, and also to develop strategies to modulate the microbial populations through foods and dietary supplements. One such strategy is the use of prebiotics, defined as 'selectively fermented ingredients that result in specific changes, in the composition and/or activity in the GI microbiota, thus conferring benefit(s) upon host health. Many dietary fibres, including RS, may fit the description of prebiotics, not only because of their ability to increase numbers of traditionally recognized bacterial markers of prebiosis (*Lactobacillus* spp. and *Bifidobacterium* spp.; also commonly used as probiotics) but also because of an ability to alter numbers of other microbes with emerging roles in health. The present invention shows that OPP, like RS, can alter numbers of some gut bacteria that were targeted for Q-PCR analysis because of their potential to impact gut health. OPP increased numbers of *Faecalibacterium prausnitzii*, a key butyrate-producer with independent anti-inflammatory activity. Numbers of some bacteria that appear to have important roles in gut mucus barrier turn-over (and potentially gut barrier integrity) were also increased by OPP. These bacteria, *Akkermansia muci-* niphila and *Ruminococcus gnavus*, are low in the large bowel of individuals with inflammatory bowel disease and in children with autism (many of whom have GI problems). Like OPP, HAMS increased numbers of *A. muciniphila*. However, HAMS increased numbers of a different *Ruminococcus* species associated with mucus, namely *Ruminococcus torques*. Also, unlike OPP, HAMS did not significantly increase numbers of the butyrate-producer *F. prausnitzii* but did increase numbers of the *Clostridium leptum* group, which contains many butyrate-producing bacteria. Some members of the genus *Roseburia* can also produce butyrate, and interestingly numbers of this genus were down in response to HAMS but not affected by OPP.

While many of the effects observed in response to OPP suggest that fibre is playing a central role, it is not possible to eliminate significant roles for polyphenols or other components of the OPP extract. GT was included as a treatment in this investigation as it is a well known source of polyphenols and has been demonstrated to have numerous beneficial biological impacts in vivo, including anti-microbial effects against some gut pathogens. However, GT generally had little effect on the gut health markers examined when compared to the WD treatment and GT did not replicate the effects seen with OPP. Interestingly, only the GT treatment increased numbers of *Lactobacillus*, suggesting some benefit to the gut and that GT and OPP polyphenols differ substantially in their characteristics and biological effects.

The effects observed suggest the route of OPP administration (food or drink) can influence physiological outcomes. Both routes of administration were designed to deliver similar doses of OPP based on calculations of intakes and levels of inclusion for the drink or food. The reasons for our finding of generally greater effects with the drink form of OPP administration can only be speculated upon. One possibility is that incorporation of OPP into the food matrix hinders its availability to microbes and tissues within the large bowel to a greater degree than occurs for the liquid form. This should be taken into consideration in developing any dietary treatments that incorporate OPP or its constituents.

Hence, it was examined that consuming a polyphenol-rich extract of the fruit, from a vegetation by-product of oil processing, which also contains fibre, has gastro-intestinal benefits in rats on a western-type diet (WD) containing 25% cooked red meat and 7% fat. The oil palm preparation (OPP) was added to food (OPP-F) or drinking water (OPP-D) to provide 50 mg gallic acid equivalents (GAE)/d and compared to effects of adding high amylose maize starch (HAMS; 30%) or green tea extract (GT; 50 mg GAE/d) to food over 4 wk. OPP treatments induced some significant effects ($P<0.05$) relative to WD alone. OPP-D increased cecal digesta mass ($3.42\pm0.37$ g v $1.86\pm0.17$ g), cecal digesta concentrations of total SCFA ($69.3\pm2.9$ mmol/kg v $53.3\pm4.5$ mmol/kg), acetate and propionate (OPP-F increased cecal butyrate concentration), numbers of mucus-producing goblet cells per colon crypt ($9.5\pm0.6$ v $6.3\pm0.6$), and cecal digesta numbers of some bacteria which may provide benefit to the host (*Faecalibacterium prausnitzii*, *Akkermansia muciniphila* and *Ruminococcus gnavus*). GT had minimal impact but did increase numbers of *Lactobacillus*. The pattern of observed effects of dietary OPP suggests that it provides a benefit to the large bowel which may be mediated by fermentation of the fibre component.

In summary, consumption of OPP can influence several markers of large bowel health that are indicative of benefit.

As will be readily apparent to those skilled in the art, the present invention may easily be produced in other specific forms without departing from its essential characteristics. The present embodiments is, therefore, to be considered as merely illustrative and not restrictive, the scope of the invention being indicated by the claims rather than the foregoing description, and all changes which come within therefore intended to be embraced therein.

The invention claimed is:

1. A method for amelioration of colon disorders by administering a therapeutically effective amount of a composition comprising oil palm polyphenolics (OPP) and fibres extracted from the vegetation liquor produced during the milling and extraction of oil from an oil palm fruit of *Elaeis guineensis*, American oil palm *Elaeis oleifera* or combinations thereof, wherein the therapeutically effective amount of the composition is a minimum 50 mg gallic acid equivalents (GAE), wherein the composition is administered along with food or with drinking water.

2. The method according to claim 1, wherein the composition increases acetate, propionate and cecal butyrate concentration in large intestine of a patient.

3. The method according to claim 1, wherein the composition increases a number of cecal digesta bacteria in large intestine of a patient, wherein the bacteria are *Faecalibacterium prausnitzii*, *Akkermansia muciniphila* and *Ruminococcus gnavus*.

* * * * *